United States Patent [19]

Rawson et al.

[11] 4,222,391

[45] Sep. 16, 1980

[54] UNITARY DISPOSABLE SANITARY SHEATH FOR TEMPERATURE AND RESPIRATION SENSING PROBE

[75] Inventors: Paul O. Rawson, Easton; Louis E. Nagy, Killingworth; George J. Veth, Fairfield, all of Conn.

[73] Assignee: United States Surgical Corporation, Norwalk, Conn.

[21] Appl. No.: 13,530

[22] Filed: Feb. 21, 1979

Related U.S. Application Data

[63] Continuation of Ser. No. 771,011, Feb. 22, 1977, abandoned.

[51] Int. Cl.³ .............................................. A61B 5/00
[52] U.S. Cl. ...................................... 128/736; 128/724
[58] Field of Search ................................ 128/724–726, 128/736; 73/339 R, 343 R, 343 B, 344, 362 R, 362 AR, 374; 206/212, 306; D10/57

[56] References Cited

U.S. PATENT DOCUMENTS

| D. 246,352 | 11/1977 | Dykstra | D10/60 |
|---|---|---|---|
| 1,568,550 | 1/1926 | Gotlesman et al. | 206/306 |
| 2,677,965 | 5/1954 | Saffir | 73/374 |
| 2,797,682 | 7/1957 | Kannenberg | 128/736 |
| 2,844,031 | 7/1958 | Rosenthal | 73/343 R |
| 3,053,261 | 9/1962 | Sieven | 131/187 |
| 3,215,265 | 11/1965 | Welin-Berger | 128/736 |
| 3,254,533 | 6/1966 | Tongret | 128/736 |
| 3,348,415 | 10/1967 | Ash, Jr. | 73/362 AR |
| 3,608,546 | 9/1971 | Shinn | 73/194 R |
| 3,822,593 | 7/1974 | Oudewaal | 73/343 R |
| 3,884,219 | 5/1975 | Richardson et al. | 128/736 |
| 3,968,690 | 7/1976 | Blouin et al. | 73/343 R |
| 4,036,211 | 7/1977 | Veth et al. | 128/736 |

FOREIGN PATENT DOCUMENTS

| 587261 | 4/1947 | United Kingdom | 73/343 R |
| 386622 | 6/1973 | U.S.S.R. | 128/725 |

Primary Examiner—Kyle L. Howell
Assistant Examiner—Francis J. Jaworski
Attorney, Agent, or Firm—Fleit & Jacobson

[57] ABSTRACT

A unitary disposable sanitary sheath is intended to cover a combination temperature and respiration sensing probe so as to not adversely affect the sensing properties of the probe. An elongated portion is provided having very thin walls to surround the temperature sensing means yet to not greatly affect its thermal conductivity characteristics. A cup-like scoop is provided to channel the respiration exhalation into the probe inlet and the scoop also having a flattened portion which is located at the place normally clasped by a patient's lips to prevent rotation of the probe and sheath during a measurement operation.

11 Claims, 9 Drawing Figures

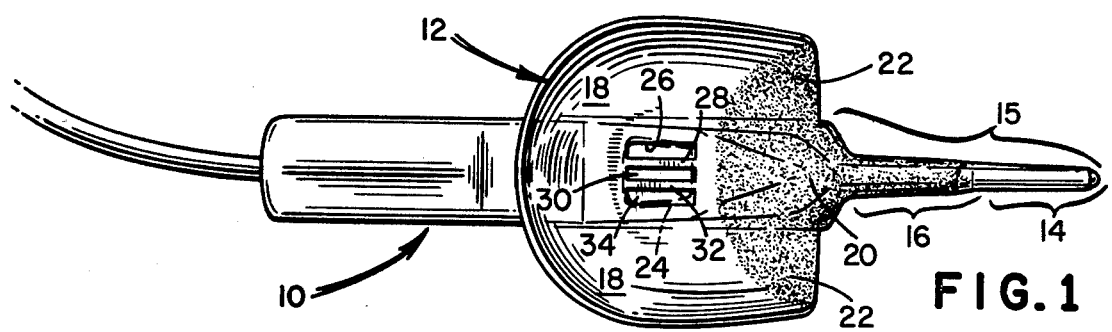
FIG. 1
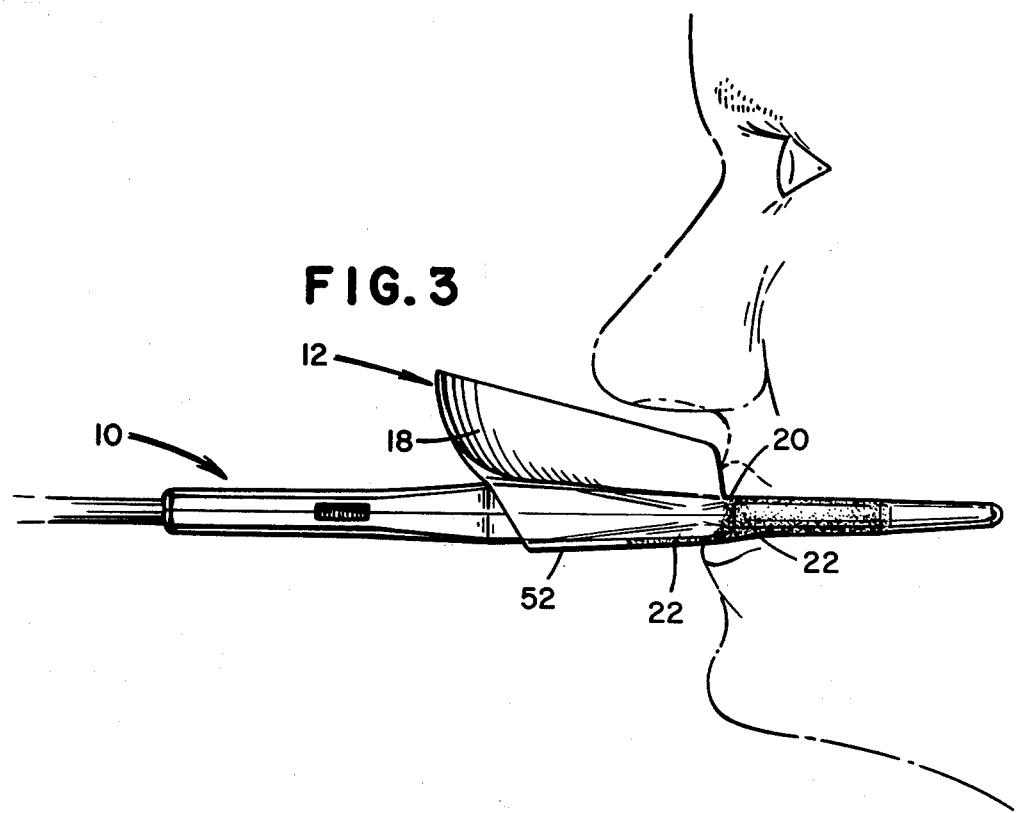
FIG. 3
FIG. 4
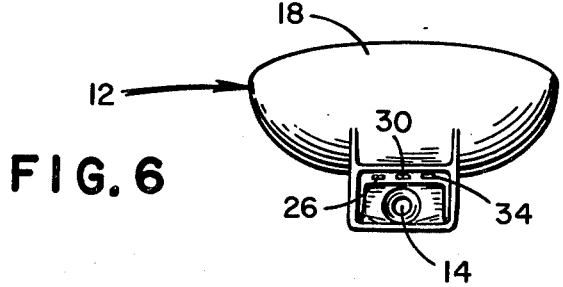
FIG. 6

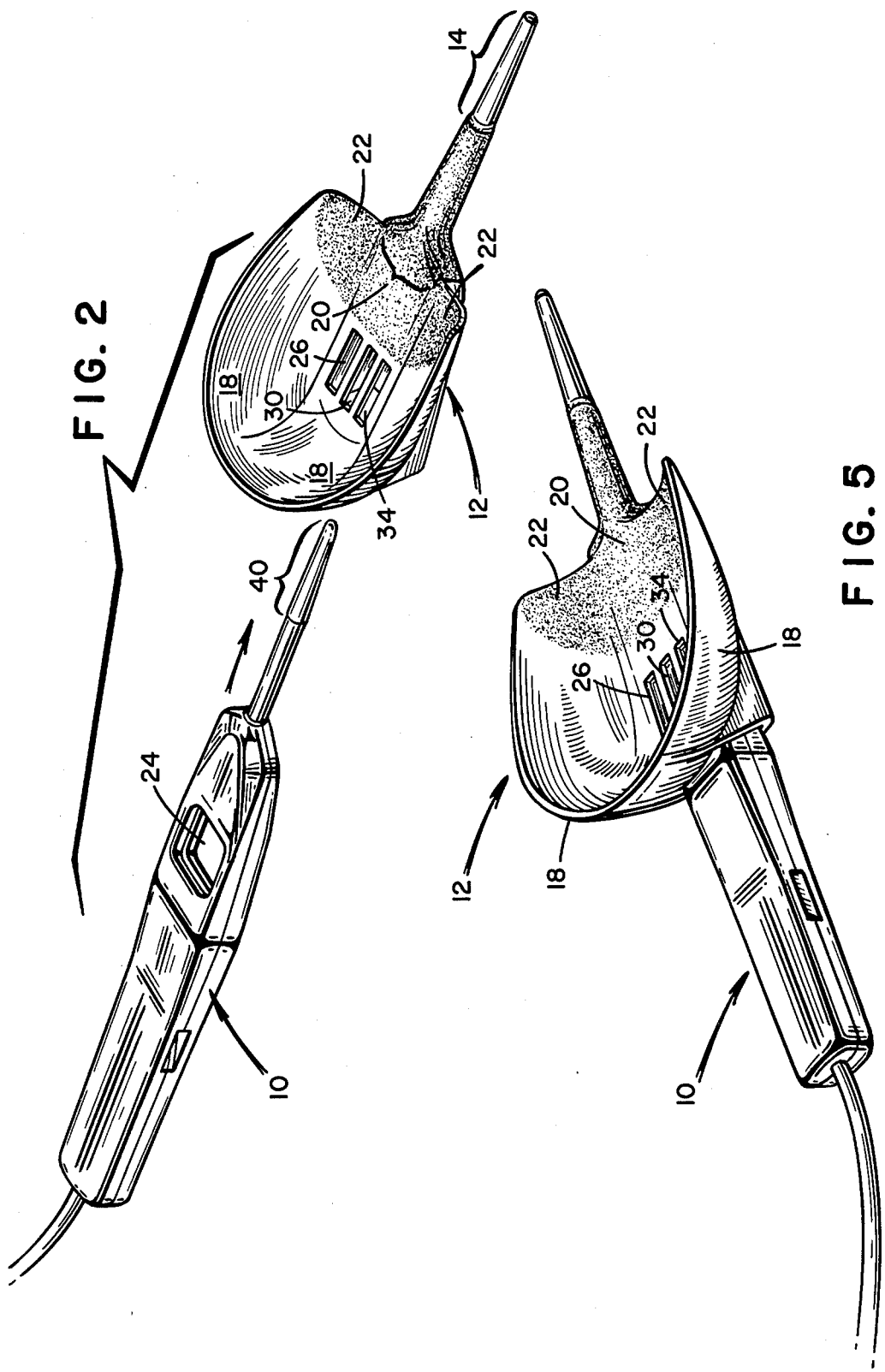

UNITARY DISPOSABLE SANITARY SHEATH FOR TEMPERATURE AND RESPIRATION SENSING PROBE

This is a continuation of application Ser. No. 771,011, filed Feb. 22, 1977 now abandoned.

BACKGROUND OF THE INVENTION

The present invention relates to a specialized disposable sanitary cover or sheath which is intended for use in surrounding a reuseable temperature and respiration sensing probe used in measuring these physiological parameters in a patient. The cover is formed in unitary construction and has a specially adapted end portion for surrounding the temperature sensing element and a specially constructed scoop portion for guiding and channeling the respiration exhalation from the patient towards the respiration sensing means located in the probe.

In keeping with the recent trend in the health care field towards automation of previous manual or mechanical sensing operations, the use of electrical sensors to measure certain patient physiological parameters has been increasing. However, such electrical sensors do not readily lend themselves to previous methods of sanitation when it is desired to use the sensor on a successive number of patients. For example, after measuring a patient's temperature with a glass-bulb thermometer, the thermometer was typically immersed in alcohol, thereby providing the necessary hygiene. However, in the case of an electronic thermometer, the physical construction of the sensing means is often adversely affected by its immersion in alcohol. Similarly, when sensing a patient's respiration rate by the use of an electronic means such apparatus must necessarily be close to the patient's face while exhaled air from the nasal passages is conducted over a suitable sensor. Accordingly, the respiration sensing means must also be cleaned in order to be used by a successive number of patients. One solution to the problem of cross-contamination between patients has been to discard the entire sensing apparatus after its initial use by a patient; however, this is expensive and has not met with much approval in the health care industry. A much better solution to the sanitation problem is the use of disposable covers or sheaths which fit over the sensing means and are discarded after each patient's use. However, such covers, while solving the problem of cleaning the sensing means, have also introduced their own peculiar problems. For example, because the thermistor which senses the temperature should be in good thermal contact with the area to be measured, the probe cover must be a good thermal conductor. The probe and cover together must have a small thermal mass to prevent adversely affecting the temperature of the body in immediate proximity to the temperature sensor.

To simultaneously measure a patient's respiration as well as temperature, it is necessary to channel the exhalations of the patient into the area where the respiration sensor is located.

A drawback of known sensing sheaths has been a tendency to become disoriented when inserted in a patient's mouth. That is, since most probes and their sheaths are rounded, the probe will often tend to rotate about its longitudinal axis after insertion in a patient's mouth, losing its desired orientation and its ability to capture the patient's respiratory exhalations and in this manner a faulty reading is likely to occur.

SUMMARY OF THE INVENTION

It is therefore an object of the pesent invention to provide a unitary sanitary sheath for covering a combined temperature and respiration sensing probe which will not adversely affect the measuring characteristics of the sensors.

It is another object of the present invention to provide a unitary sanitary cover for a patient physiological parameter sensing probe which has a tapered end portion at the area intended for contact with the temperature sensing portion of the probe so as to improve the heat transfer characteristics between the thermistor and the patient.

It is a further object of the present invention to provide a unitary sanitary sheath for a temperature and respiration sensing probe having a large scoop like area to collect and deflect the exhalations of the patient to the respiration sensing means.

It is a still further object of the present invention to provide a disposable unitary sanitary cover for a temperature and respiration sensing probe which has a substantially flat area located at the place on the sheath corresponding to the location where the patient will clasp his lips around the probe.

Finally, it is an object of the present invention to provide a disposable, unitary, sanitary, sheath for a temperature and respiration sensing probe which has only a relatively thin portion covering the temperature sensing means and has a relatively large scoop to direct the respiration exhalations to the respiration sensing means and which has a flat portion corresponding to the place where a patient will grasp the probe and sheath combination with his lips wherein the flat portion is partially roughened so as to eliminate any slippery sensation to the patient.

These and other objects are achieved by the present invention by providing a one piece plastic sheath which may be formed by injection molding, and which has a substantially thin tapered portion at the area which is intended to mate with the temperature sensing means of the temperature and respiration sensing probe, and which has a large scoop-like contoured surface located in the vicinity of the inlet port for the respiration rate determination means. This scoop-like area is provided to channel the exhalations of the patient, so as to direct them into contact with the sensing means which is located in the interior of the probe. The unitary sheath of the present invention is also provided with a flat area corresponding to the location of the patient's lips so that upon grasping the sensor in the patient's mouth, it will have no tendency to rotate about the longitudinal axis of the probe. Finally, since it is very often the case that the plastic choosen to construct the sheath of the present invention may be a polyethylene type which is rather slippery when wet, the area where the patient's lips will contact the sheath may be slightly roughened thereby permitting the patient to gain a better purchase on the cover.

BRIEF DESCRIPTION OF THE DRAWINGS

FIG. 1 is a plan view of the top of a temperature and respiration sensing probe located within a unitary cover provided by the present invention.

FIG. 2 is an exploded perspective view of a temperature and respiration sensing probe aligned with, but withdrawn from, the unitary, disposable, sheath of the present invention.

FIG. 3 is a side view a temperature and respiration sensing probe inserted in the unitary disposable sheath of the present invention and showing the face of a typical patient in phantom.

FIG. 4 is a view from the bottom of a temperature and respiration sensing probe inserted in the sheath.

FIG. 5 is a perspective view taken from the rear of a sensing probe and sheath combination.

FIG. 6 is an elevation view taken from the rear of the disposable hygenic sheath of the pesent invention.

DETAILED DESCRIPTION OF THE PREFERRED EMBODIMENT

Figure 7:
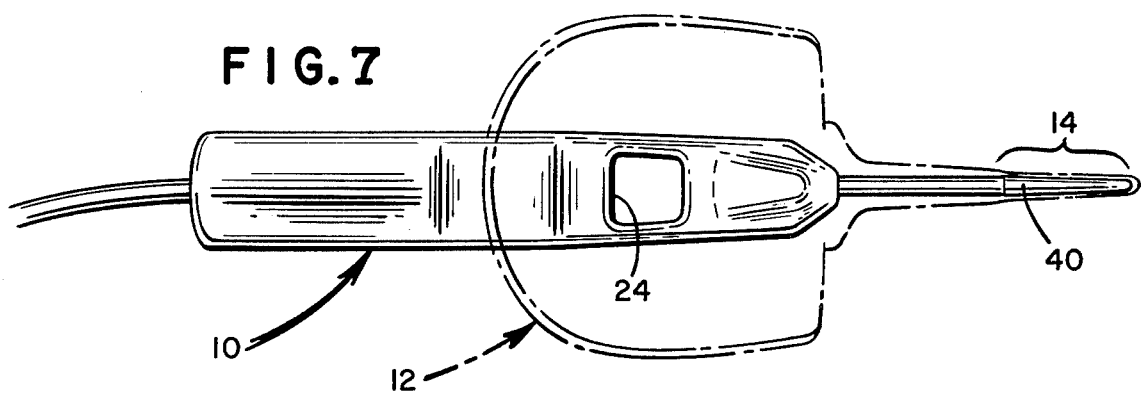
FIG. 7 is a view of a portion of the sensing probe and showing the sheath in phantom.

FIG. 1 shows a suitable temperature and respiration sensing probe at 10 inserted into the sheath 12 of the present invention. The elongated temperature sensing tip 15 is inserted in the patient's mouth and the temperature sensing tip of the probe 14 is placed under the tongue. The portion of the sheath at 14 is intended to be substantially thinner than the rest of the sheath including portion 16. Sheath tip 14 has a conical taper, and fits in intimate contact with the temperature sensing tip 40 as shown in FIG. 2 of the probe 10 and is essentially the same length as section 14. Also shown in FIG. 1 is the curved scoop portion 18 for collecting and directing air expired through the patient'nose. A flat area 20 is provided on the upper surface of the sheath to orient the sheath with scoop 18 toward the nose as the patient's lip rests on area 20. A textured surface may be provided at 22 generally covering the flat area 20.

Figure 8:
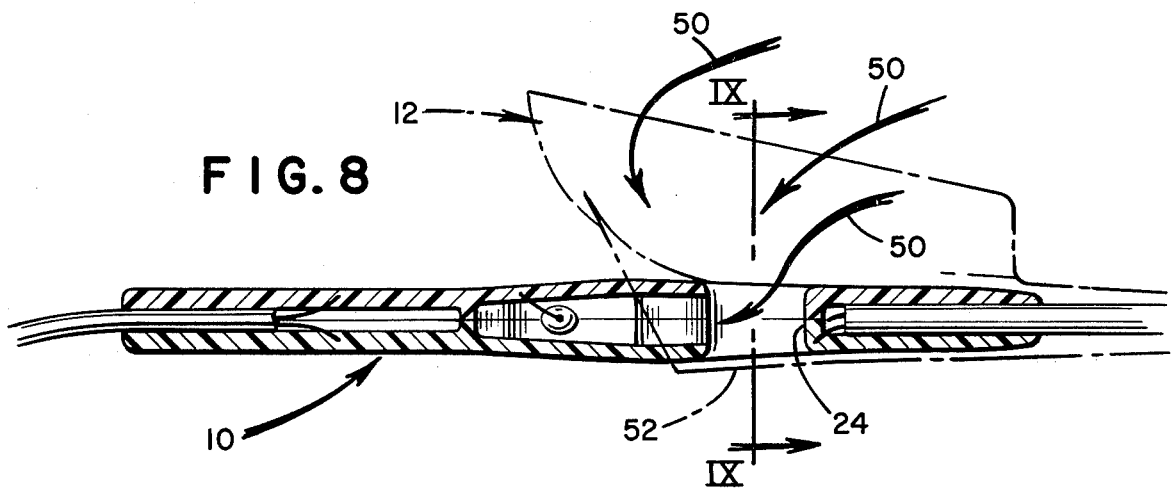
FIG. 8 is a longitudinal sectional view of the sensing probe showing the sheath of the present invention in phantom.

To permit the exhalation from the patient to be introduced into the probe housing, sheath 12 provides openings 26, 30 and 34 which communicate with the inlet aperture 24 of the probe 10, as shown in FIGS. 2 and 8. Multiple small openings are provided so that when inserting the probe 10 into the sheath 12 the temperature sensing portion of probe 10 will not exit improperly, as it might through a single large hole. Accordingly, the slats or bars 28 and 32 will direct the conical tip 40 of the temperature sensor 10 into the tip of the sheath 12. This insertion is suggested in FIG. 2.

FIG. 2 shows a suitable temperature and respiration sensing probe 10 in a position for insertion into the unitary sheath 12, the cup-like scoop 18 of the sheath 12, and the textured flat surface 22 intended to be grasped by the patient's upper lip. The slots cut into the sheath will not allow the conical tip of sensor 40 from exiting through the slots.

In FIG. 3 the flat portion 20 of the probe cover 12 is grasped by the patient's lips and the textured surface 22 will be in contact with the lip. Scoop 18 is shown located directly below the patient's nasal passages where it will be in the path of most of the patient's exhaled air.

FIG. 4 shows the bottom of a sheath having a probe inserted therein. The sheath may be made of poyethelene or polypropylene plastic. The inlet aperture 24 of the probe 10 is shown within the sheath and covered on one side by the bottom 52 also shown in FIG. 8 of sheath 12.

FIG. 5 shows the assembled probe and sheath from the rear including the scoop 18, which surrounds the slots provided to permit the flow of exhaled air into the probe respiration sensor.

FIG. 6, a rear view of the sheath of the present invention, shows the scoop 18 and also the slots 26, 30 and 34. Looking into the rear of the sheath the thin conical tip 14 for temperature sensing may be seen.

In FIG. 7, the thin tip 14 of the probe 10 extends for a distance which is equal to the length of the metallic tip 40 of the temperature sensor of probe 10. It is this thin portion which is made to have an inner diameter which is slightly less than the outer diameter of the metal portion 40 so that upon insertion of the probe into the sheath the two portions will be brought into intimate contact.

In FIG. 8 the unitary cover is shown in combination with the probe for which it is intended to be used and in this view it may be seen that the exhaled air, shown generally by the arrows 50, is caused to enter the slots which are in communication with the inlet port 24 of the probe.

Figure 9:
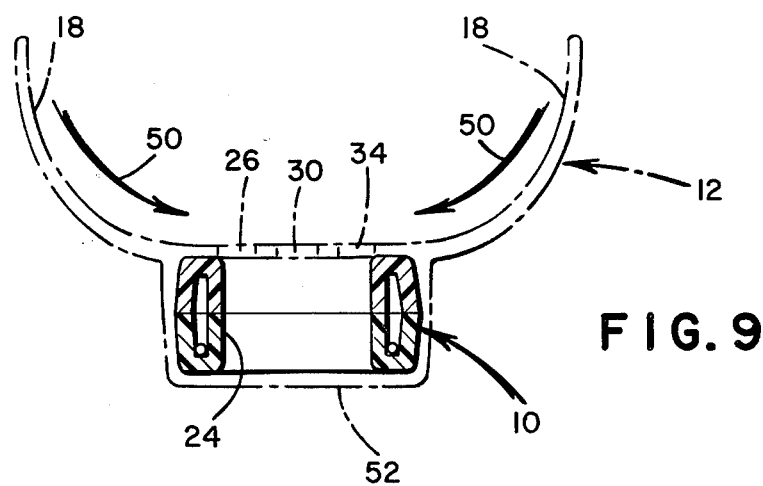
FIG. 9 is a transverse cross-section of the temperature and respiration sensing probe of FIG. 8 taken along line IX and showing the unitary sheath of the present invention surrounding the probe.

FIG. 9 shows the sheath of the present invention surrounding the probe 10 and the manner in which the openings 26, 30 and 34 permit exhaled air to flow into the inlet aperture 24 of the probe 10. Also shown in this view is the manner in which one opening of the transversely arranged inlet aperture 24 of probe 10 is covered by the bottom 52 of sheath 12 so that the exhaled air does not pass through the probe housing but rather is caused to be directed into the passage containing the respiration sensing means.

It is, of course, understood that the preceeding description was only given by way of example and that various other forms may be taken by the unitary sheath of the present invention.

What is claimed is:

1. A unitary disposable sanitary sheath for use with a temperature and respiration probe, comprising an elongated tube having a closed front end, an open and hollow rear end having an interior for insertion of a portion of said probe into said sheath, and a tapered portion extending rearwardly from said front end to said open and hollow rear end, the walls of said tapered portion being substantially thinner than the remainder of the sheath;

said tube further comprising an upper surface disposed rearwardly of said tapered portion, said upper surface forming a cup-like scoop opening upwardly from said surface of said tube;

said upper surface being discontinuous so as to form at least one respiration inlet aperture therein, said at least one respiration inlet aperture being in fluid communication with said temperature and respiration probe via the interior of said open and hollow rear end of said tube when said probe portion is inserted into said sheath;

whereby, upon insertion of said probe portion into said sheath, and insertion of said probe portion and sheath into a patient's mouth, air expired through the patient's nose is collected and directed by said scoop into and through said at least one respiration inlet aperture.

2. The sheath of claim 1, comprising a substantally flat transition area provided with a textured surface at the location of a patient's lips during a temperature and respiration sensing operation so as to be rough relative to the remaining surface of the probe.

3. The sheath of claim 1, wherein said probe portion and said tapered portion are substantially conical in shape and decreasing in diameter, and wherein the decreasing conical inner diameter of said tapered portion is at all corresponding points less than the decreasing conical outer diameter of the probe portion.

4. The sheath of claim 1, wherein said at least one respiration inlet aperture comprises a plurality of bars and slots, said slots permitting respiration to pass therethrough and said bars prohibiting said probe from entering said respiration inlet aperture during said insertion of said probe portion into said sheath.

5. The sheath of claim 1, wherein said cup-like scoop is arranged in such relation to said elongate tube, and said transition area is of such size, that when said probe portion and said sheath are inserted in a patient's mouth said cup-like scoop is disposed substantially beneath said patient's nose, whereby said scoop collects and directs air expired through said patient's nose to said respiration inlet aperture.

6. A disposable sanitary sheath for use with a temperature and respiration sensing probe, said sheath comprising:
   an elongated tubular portion having a thin-walled tapered portion at a closed end thereof,
   a hollow transition portion being substantially rectangular in cross section and being joined to said elongated tubular portion so as to be in communication with the interior thereof, said transition portion being arranged so that the longer sides of the rectangle form the top and bottom surfaces of the sheath,
   a hollow rear portion being joined to said hollow transition portion so that the interiors of said hollow rear portion and said hollow transition portion are in communication and having an opening for insertion of said probe into said sheath,
   a cup-like scoop portion having curved walls joined to a top surface of said rear portion and having an open top area facing upwardly and an open front area facing toward said hollow transition portion, and
   a respiration inlet aperture arranged substantially horizontally and disposed at the bottom of said cup-like scoop and extending through the top surface of said hollow rear portion,
   whereby upon insertion of said probe into said sheath and said probe and sheath into a patient's mouth, air expired through the patient's nose is collected and directed by said scoop into and through said respiration inlet aperture.

7. The sheath of claim 6 wherein said thin tapered portion of said elongated tubular portion is formed as a truncated cone mating with the temperature sensing portion of said temperature and respiration sensing probe, wherein said truncated cone has a decreasing conical diameter which is less than the decreasing conical diameter of said temperature sensing portion at all corresponding points, whereby upon insertion of said temperature and respiration sensing probe into said sheath, said temperature sensing portion and said truncated cone portion of said elongated tubular portion are in tight-fitting contact.

8. The sheath of claim 6 further comprising bars arranged to span said respiration inlet aperture thereby forming said aperture into a plurality of slots, whereby said slots permit the passage of said air expired through the patient's nose and said bars prevent said probe from entering said aperture during insertion of said probe into said sheath.

9. The sheath of claim 6 wherein the external surface of said hollow transition portion at the location occupied by a patient's lips during use of said sheath is formed having a roughened texture relative to the surface textures of said elongated tubular portion and said hollow rear portion.

10. The sheath of claim 6 wherein said cup-like scoop portion has a curved rear wall portion which extends upwardly so as to direct the air expired through the patient's nose into said respiration inlet aperture.

11. The sheath of claim 6 wherein said elongated tubular portion, said hollow transition portion, said hollow rear portion and said curved scoop portion are all formed as a unitary sheath being composed of polyethylene.

* * * * *